United States Patent [19]

Matsunaga et al.

[11] Patent Number: 4,517,387
[45] Date of Patent: May 14, 1985

[54] PROCESS FOR PRODUCTION OF 2,2-BIS(4-HYDROXYPHENYL) PROPANE

[75] Inventors: Fujihisa Matsunaga; Tadahiko Nishimura, both of Iwakuni; Etsuo Miyake; Kiyotaka Banba, both of Wakayama, all of Japan

[73] Assignees: Mitsui Petrochemical Industries, Ltd.; Honshu Chemical Ind. Co. Ltd., both of Tokyo, Japan

[21] Appl. No.: 536,029

[22] Filed: Sep. 26, 1983

[30] Foreign Application Priority Data

Sep. 30, 1982 [JP] Japan ............................ 57-169858
Sep. 30, 1982 [JP] Japan ............................ 57-169859
Sep. 30, 1982 [JP] Japan ............................ 57-169860

[51] Int. Cl.$^3$ .......................................... C07C 39/16
[52] U.S. Cl. .................................................. 568/728
[58] Field of Search ...................................... 568/728

[56] References Cited

U.S. PATENT DOCUMENTS

| 2,730,552 | 1/1956 | Williamson | 568/728 |
| 2,791,616 | 5/1957 | Luten | 568/728 |
| 2,923,744 | 2/1960 | Scriabine et al. | 568/728 |
| 2,936,272 | 5/1960 | Bender et al. | 568/728 |
| 3,264,357 | 8/1966 | Webb et al. | 568/728 |
| 3,418,378 | 12/1968 | MacNaughton et al. | 568/728 |
| 4,192,955 | 5/1980 | Reinitz | 568/724 |
| 4,317,944 | 5/1982 | Davis | 568/728 |
| 4,408,087 | 1/1983 | Li | 568/724 |

FOREIGN PATENT DOCUMENTS 667831 3/1965 Belgium ................................ 568/728

Primary Examiner—Werren B. Lone
Attorney, Agent, or Firm—Armstrong, Nikaido, Marmelstein & Kubovcik

[57] ABSTRACT

A process for continuously producing 2,2-bis(4-hydroxyphenyl) propane having a high quality from a reaction of phenol and acetone in the presence of a hydrochloric acid containing catalyst comprising the steps of:

(A) carrying out the reaction by continuously charging additional phenol, the below-mentioned circulating phenol, additional acetone, additional hydrogen chloride or hydrochloric acid, the below-mentioned circulating oily mother liquor, and the below-mentioned aqueous mother liquid into a reactor to form a reaction mixture slurry comprising the crude phenol adduct of 2,2-bis(4-hydroxyphenyl) propane in the form of crystal and two liquid phase reaction mother liquors of an oily mother liquor and an aqueous mother liquor;

(B) separating the reaction mixture slurry into the crude phenol adduct of 2,2-bis(4-hydroxyphenyl) propane and the two liquid phase mother liquors after discharging the reaction mixture slurry from the reactor;

(C) separating the two liquid phase mother liquors obtained in the above-mentioned step (B) into the oily mother liquor and the aqueous mother liquor, whereby the oily mother liquor is circulated as a circulating oily mother liquor to the reactor and the remaining portion of the aqueous mother liquor, after discharging a portion thereof, is circulated as a circulating aqueous mother liquor to the reactor;

(D) dissolving the crude phenol adduct of 2,2-bis(4-hydroxyphenyl) propane obtained in the above-mentioned step (B) in a phenol solvent and, after neutralizing the hydrogen chloride or hydrochloric acid contained in the crude phenol adduct with a base, crystallizing and separating the phenol adduct of 2,2-bis(4-hydroxyphenyl) propane from the solution to obtain the purified phenol adduct of 2,2-bis(4-hydroxyphenyl) propane;

(E) decomposing the purified phenol adduct of 2,2-bis(4-hydroxyphenyl) propane obtained in the above-mentioned step (D), on heating, to form a thermally decomposed product containing phenol and 2,2-bis(4-hydroxyphenyl) propane;

(F) recovering the phenol and 2,2-bis(4-hydroxyphenyl) propane from the thermally decomposed product obtained in the above-mentioned step (E); and (G) circulating the phenol recovered in the above-mentioned step (F) to the reactor in the above-mentioned step (A) as a circulating phenol or to the above-mentioned step (D) as a phenol solvent.

6 Claims, 2 Drawing Figures

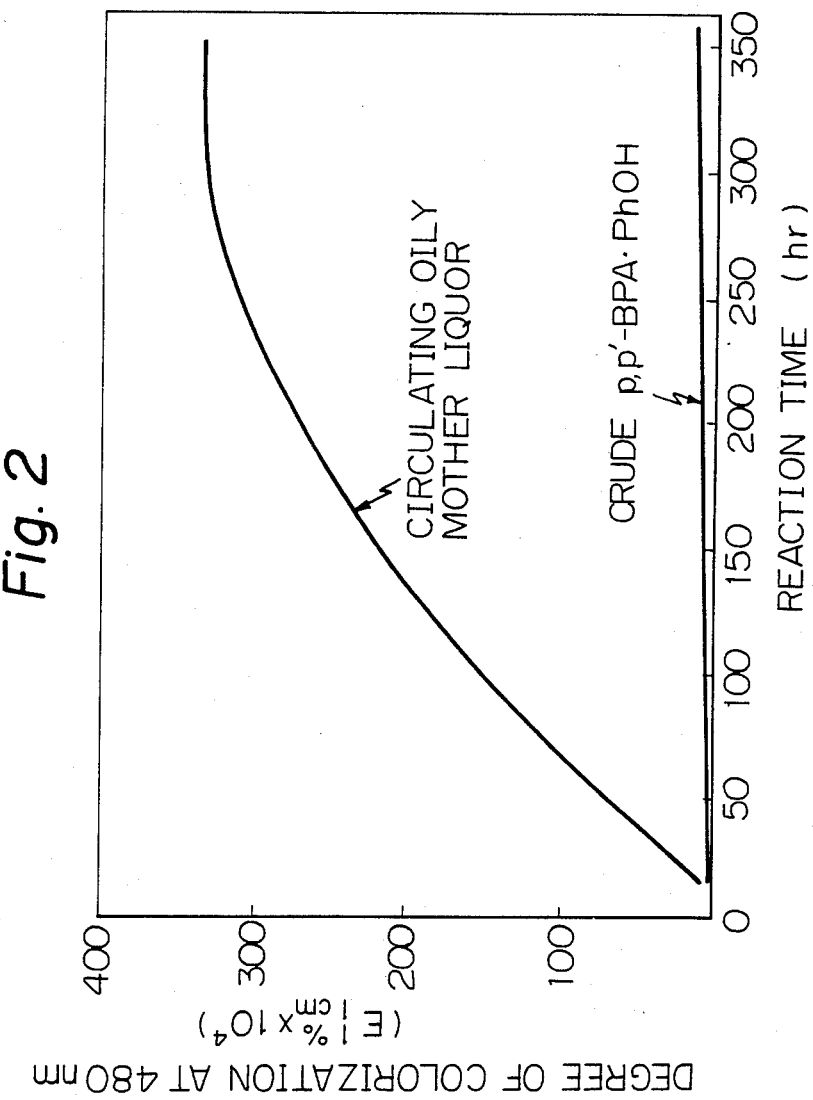

PROCESS FOR PRODUCTION OF 2,2-BIS(4-HYDROXYPHENYL) PROPANE

BACKGROUND OF THE INVENTION

1. Field of the Invention

The present invention relates to a process for continuously producing 2,2-bis(4-hydroxyphenyl)propane ("p,p'-BPA" hereinbelow) having a high quality from a reaction of phenol and acetone in the presence of a hydrochloric acid catalyst. More specifically, it relates to a process for continuously and economically producing p,p'-BPA having a high quality at a high yield to the reacted phenol and acetone.

2. Description of the Prior Art p,p'-BPA has heretofore been used as a starting material for the production of polycarbonate or epoxy resins. Recently, the high quality resins have been coming into increased demand and have been used for a wider range of applications. As a result, higher quality resins have been required in the art. Along with this, a higher quality product of p,p'-BPA having a high purity and good color has come into demand as a starting material of these resins. Especially, a high quality p,p'-BPA having, for example, a purity of 99.9 mole % or more and APHA color of a molten product of 30 or less has been demanded as a starting material for polycarbonate. Furthermore, it is also required to economically produce a high quality p,p'-BPA. In order to fulfill these requirements, it is necessary to selectively produce p,p'-BPA by reacting starting phenol and acetone at a high one-pass conversion.

Furthermore, the resultant p,p'-BPA should be readily purified and a high quality p,p'-BPA should be produced at a high yield and low cost. More specifically, when the starting phenol and acetone are reacted in the presence of an acid catalyst, various by-products are also produced in addition to the desired p,p'-BPA. Examples of such by-products are isomeric by-products such as 2-(2-hydroxyphenyl)-2-(4-hydroxyphenyl)propane ("o,p'-BPA" hereinbelow) and 2,2-bis(2-hydroxyphenyl)propane ("o,o'-BPA" hereinbelow); high boiling point by-products such as 4-(4-hydroxyphenyl)-2,2,4-trimethylchroman ("co-dimer" hereinbelow), 2,4-bis(α,α-dimethyl-4-hydroxybenzyl)phenol ("BPX" hereinbelow), 2-(2-hydroxyphenyl)-2,4,4-trimethylchroman ("o-dimer" hereinbelow), 5-hydroxy-3-(4-hydroxyphenyl)-1,3,3-trimethylindane ("IPEP cyclic dimer" hereinbelow), and 2,4-bis(4-hydroxyphenyl)-4-methyl-1-pentene ("IPEP linear dimer" hereinbelow); and other colored unknown structure by-products. Therefore, those by-products capable of being converted to p,p'-BPA must be readily and efficiently converted to p,p'-BPA.

Heretofore, many processes for producing p,p'-BPA by reacting phenol and acetone in the presence of an acidic catalyst have been proposed. For example, the use of hydrogen chloride or hydrochloric acid as a catalyst in the reaction of phenol and acetone and the purification and separation of the desired p,p'-BPA from the resultant reaction product derived from the above-mentioned reaction are disclosed in, for example, Japanese Examined Patent Publication Nos. 27-5367, 36-23335, 38-4875, 40-7186, 42-6333, 43-3379, 47-10384, and 50-12428 and Japanese Unexamined Patent Publication Nos. 48-97853, 49-93347, 49-82651, 53-101347, 54-98748, and 54-98749.

However, these proposed processes have had problems in that a large amount of the above-mentioned by-products including isomeric by-products, high-boiling point by-products, and colored by-products are formed when p,p'-BPA is produced according to the processes disclosed in the above-mentioned publications. The formation of the by-products decreases the selectivity of the reaction to the desired p,p'-BPA. Furthermore, the quality of the desired product is decreased and the purification of the desired product becomes difficult due to the contamination thereof with the by-products. Consequently, the desired p,p'-BPA having a high quality cannot be economically produced at a high yield and a high selectivity according to the above-mentioned processes. Furthermore, when the purification and separation methods disclosed in the above-mentioned publications are used for treating the reaction mixture obtained from the above-mentioned catalytic reaction, the removal of the above-mentioned by-products is difficult. Therefore, high-quality p,p'-BPA cannot be selectively and economically produced at a high yield.

For example, of the above-mentioned prior publications in which the intended reaction are carried out in the presence of hydrogen chloride or hydrochloric acid as a catalyst, Japanese Examined Patent Publication No. 42-6333 proposes a process for the production of p,p'-BPA from phenol and acetone in which p,p'-BPA is recovered from the by-products (i.e., resinous by-products) after removing p,p'-BPA from the reaction product of phenol and acetone. The by-products and phenol are treated in the presence of hydrogen chloride or hydrochloric acid to improve the substantial selectivity of the reactants to p,p'-BPA and the yield of p,p'-BPA and, then, the resultant p,p'-BPA is recovered from the reaction mixture. However, according to this proposed process, the p,p'-BPA is first separated from the reaction mixture obtained by the reaction of phenol and acetone in the presence of hydrogen chloride or hydrochloric acid. The treatment of the by-products thus obtained and the condensation reaction of acetone and phenol are also carried out in separate reactors according to the above-mentioned process. This complicates the reaction systems and, further, increases the amounts of the by-products to be treated in the isomerization reaction. Since the isomerization reaction of the by-products into the desired p,p'-BPA is limited to the equilibrium composition, the isomerization efficiency of the by-products into p,p'-BPA becomes low. Consequently, the overall selectivity to the desired p,p'-BPA and the overall yield of the desired p,p'-BPA are low and the desired p,p'-BPA cannot be economically produced.

Furthermore, of the above-mentioned prior publications disclosing the use of hydrogen chloride or hydrochloric acid in the preparation reaction of p,p'-BPA, Japanese Examined Patent Publication No. 42-26787 discloses a process for producing p,p'-BPA having a high purity from a mixture obtained by removing hydrogen chloride from the reaction mixture after the completion of the reaction. According to this process, hydrogen chloride gas is removed from the reaction mixture by treating the reaction mixture under a reduced pressure (or in vacuo) without heating or bubbling an inert gas into the reaction mixture and, then, the phenol adduct of p,p'-BPA ("p,p'-BPA.PhOH" hereinbelow) is crystallized from the resultant mixture, followed by the decomposition of the p,p'-BPA.PhOH. Thus, p,p'-BPA is recovered.

In a specific embodiment thereof, it is described that the reaction mother liquor separated from the p,p'-BPA.PhOH by filtration can be circulated to and used in the reactor. However, this process is still disadvantageous in that p,p'-BPA having a high purity cannot be economically produced. That is, the formation of hydrochloric acid should be suppressed in the reaction system in order to effectively remove the hydrogen chloride from the reaction mixture and, therefore, as is clear from the examples of the above-mentioned publication, the conversion of the starting acetone in the reaction should be maintained to as low as about 50% or less to minimize the amount of water formed by the reaction and the effective reutilization of the hydrogen chloride is substantially difficult even if the reaction mother liquid is recycled since the substantial amount of the hydrogen chloride gas is removed from the reaction mother liquor.

In addition, the comparative tests in Example 1 of Japanese Examined Patent Publication No. 42-26787 discloses that p,p'-BPA is recovered from an organic phase derived from the neutralization of the reaction mixture with a caustic soda solution. However, according to this process, the quality of the resultant p,p'-BPA is poor and a hydrogen chloride catalyst cannot be reused upon circulation.

Furthermore, many proposals relating to the use of acidic ion exchange resins or the modified products thereof as a catalyst during the reaction of phenol and acetone and the purification and separation of p,p'-BPA from the reaction product so obtained are disclosed in, for example, Japanese Examined Patent Publication Nos. 36-23334, 37-14721, 37-981, 41-4454, 45-10337, 46-19953, 48-71389, and 49-48319 and Japanese Unexamined Patent Publication Nos. 52-42861, 54-19951, and 54-19952.

However, in order to sufficiently effect the desired catalytic activity in the proposed processes, it is required that the concentration of p,p'-BPA.PhOH in the reaction system be maintained to a low level so as not to crystallize the p,p'-BPA.PhOH as a crystal to form a reaction mixture slurry and so as to form a homogeneous reaction mixture solution. For this reason, it is necessary to maintain the conversion of the starting acetone to 55 mole % or less or to increase the mole ratio of the phenol to the acetone in the reaction system. Accordingly, the one-pass conversions of the starting materials are low commonly in these proposed methods and, therefore, large amounts of the starting materials should be recovered from the reaction mixture and recycled to the reaction system. Thus, expensive utility costs are required for recovering and recycling the unreacted starting materials and, therefore, the desired effective and economical reaction cannot be carried out.

In addition, larger amounts of various isomer by-products, high-boiling point by-products, and colored by-products are also formed in addition to the desired p,p'-BPA in the reaction utilizing, as a catalyst, an acidic ion exchange resin, as in the case of the above-mentioned hydrogen chloride or hydrochloric acid catalyst. Various attempts to increase the yield of the desired p,p'-BPA by isomerizing the by-products to p,p'-BPA have also been proposed in these reaction processes utilizing acidic ion exchange resin catalysts.

For this purpose, for example, Japanese Examined Patent Publication No. 37-981 discloses the recycling of the remaining by-products, together with phenol and acetone, to a reactor containing the above-mentioned acidic ion exchange resin catalyst, after recovering p,p'-BPA or p,p'-BPA.PhOH and the unreacted starting materials from the reaction mixture. This patent publication also discloses that p,p'-BPA.PhOH is crystallized by cooling the resultant mixture obtained by distilling off the unreacted starting materials from the reaction mixture and, then, the reaction mother liquor containing the above-mentioned by-products after filtering-off the crystalline is recycled to the reaction mixture.

However, when the continuous reaction is carried out by circulating the reaction mother liquor containing the by-products to the reactor according to the disclosed process, the disadvantages of the above-mentioned processes utilizing the acidic ion exchange resin catalysts cannot be eliminated. Moreover, the by-products are accumulated in the reaction system due to low isomerization rate of the by-products in the reaction mother liquor to p,p'-BPA and, therefore, not only is the occurrence of the smooth reaction impaired, but also the desired p,p'-BPA having a high quality cannot be obtained. In addition, when a long-term continuous reaction is carried out, this phenomenon further becomes remarkable because the activity of the acidic ion exchange resin catalyst is remarkably decreased. Accordingly, this process is not advantageous for commercial production of p,p'-BPA.

SUMMARY OF THE INVENTION

Accordingly, the objects of the present invention are to eliminate the above-mentioned problems or disadvantages of the prior art and to provide a process for continuously and economically producing high quality p,p'-BPA at a high selectivity and a high yield.

Other objects and advantages of the present invention will be apparent from the following description.

In accordance with the present invention, there is provided a process for continuously producing high quality, p,p'-BPA from a reaction of phenol and acetone in the presence of a hydrochloric acid containing catalyst comprising the steps of:

(A) carrying out the reaction by continuously charging additional phenol, the below-mentioned circulating phenol, additional acetone, additional hydrogen chloride or hydrochloric acid, the below-mentioned circulating oily (or oil phase) mother liquor, and the below-mentioned aqueous (or aqueous phase) mother liquid into a reactor to form a reaction mixture slurry comprising crude p,p'-BPA.PhOH in the form of crystal and two liquid phase reaction mother liquors of an oily mother liquor and an aqueous mother liquor;

(B) separating the reaction mixture slurry into the crude p,p'-BPA.PhOH and the two liquid phase mother liquors discharging the reaction mixture slurry from the reactor;

(C) separating the two liquid phase mother liquors obtained in the above-mentioned step (B) into the oily mother liquor and the aqueous mother liquor, whereby the oily mother liquor is circulated as a circulating oily mother liquor to the reactor and the remaining portion of the aqueous mother liquor, after discharging a portion thereof, is circulated as a circulating aqueous mother liquor to the reactor;

(D) dissolving the crude p,p'-BPA.PhOH obtained in the above-mentioned step (B) in a phenol solvent and, after neutralizing the hydrogen chloride or hydrochloric acid contained in the crude p,p'-BPA.PhOH with a base, crystallizing and separating the p,p'-BPA.PhOH from the solution to obtain the purified p,p'-BPA.-PhOH;

(E) decomposing the purified p,p'-BPA.PhOH obtained in the above-mentioned step (D), on heating, to form a thermally decomposed product containing phenol and p,p'-BPA;

(F) recovering the phenol and p,p'-BPA from the thermally decomposed product obtained in the above-mentioned step (E); and (G) circulating the phenol recovered in the above-mentioned step (F) to the reactor in the above-mentioned step (A) as a circulating phenol or to the above-mentioned step (D) as a phenol solvent.

BRIEF DESCRIPTION OF THE DRAWINGS

The present invention will be better understood from the description set forth below with reference to the accompanying drawings wherein:

FIG. 2 is a graphical drawing showing a correlation between the degree of colorization at 480 nm and the reaction times of the circulating oily mother liquor and the crude p,p'-BPA.PhOH.

DESCRIPTION OF THE PREFERRED EMBODIMENTS

Figure 1:
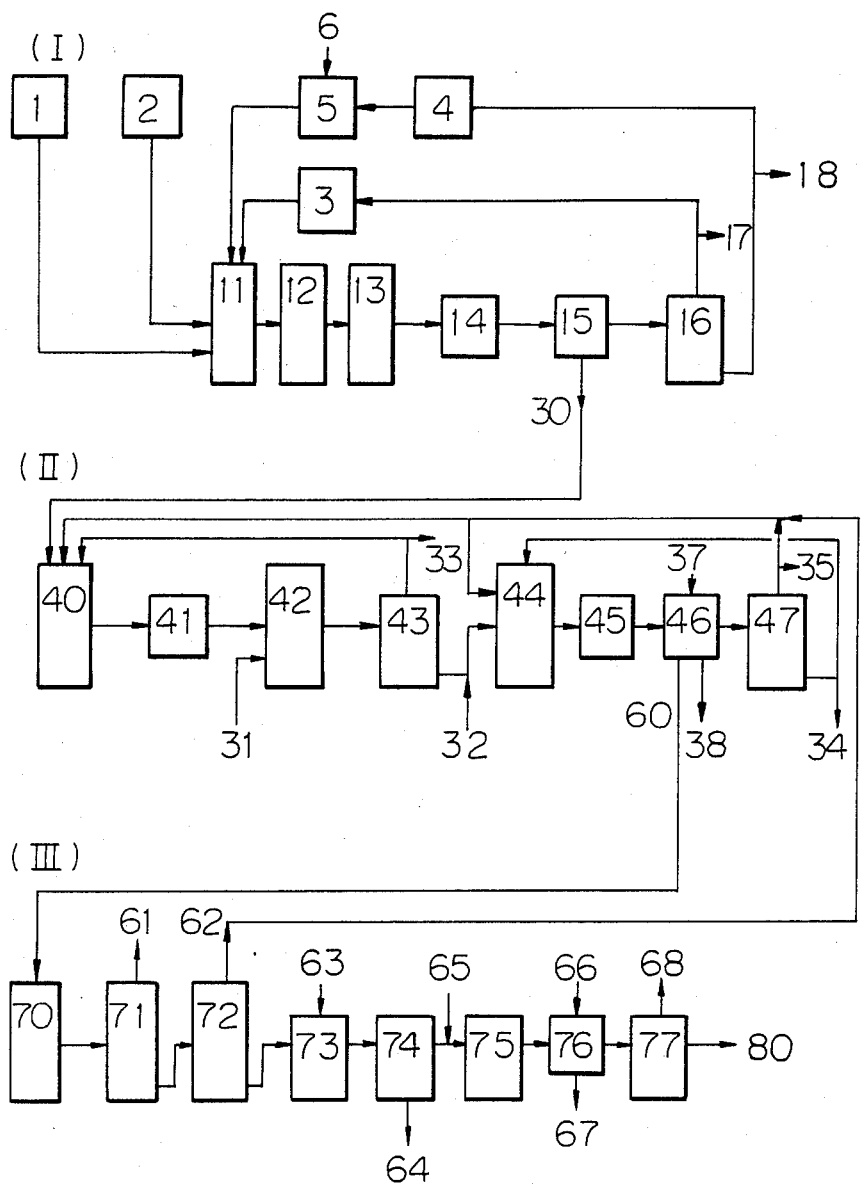
FIG. 1 is a flow diagram illustrating a mother liquor circulating type continuous condensation reaction apparatus used in one embodiment of the present invention.

According to the present invention, the desired high quality p,p'-BPA can be selectively produced at a high yield by continuously reacting phenol and acetone in the presence of a hydrochloric-acid-containing catalyst in a reactor, separating crude p,p'-BPA.PhOH crystals from the resultant reaction mixture slurry, recycling the reaction mother liquor containing mostly of the hydrochloric acid containing catalyst and by-products to the reactor, and obtaining the purified p,p'-BPA.PhOH from the neutralization and purification of the crude p,p'-BPA.PhOH crystals, followed by decomposing the purified p,p'-BPA.PhOH. Furthermore, the present invention is advantageous over any conventional process in that the hydrochloric-acid-containing catalyst contained in the reaction mother liquor can be effectively recycled to the reactor without using a distillation operation and p,p'-BPA can be effectively recovered from the recycled by-products. Thus, according to the present invention, the desired high quality p,p'-BPA can be reasonably produced at a low cost, as compared with any conventional process.

The acidic catalysts usable in the condensation reaction of phenol and acetone according to the present invention are hydrochloric acid containing catalysts. Generally, hydrogen chloride is present at a super-saturated state, together with the hydrochloric acid in the reaction system. According to the present invention, acidic catalyst consisting of hydrochloric acid, or hydrochloric acid and hydrogen chloride, can be used. Acidic catalysts containing hydrochloric acid and other co-catalyst components can also be used in the practice of the present invention. Any conventional co-catalyst can be used in the present invention. Examples of the co-catalysts usable in the present invention are sulfur containing compounds soluble in the reaction mixture. The sulfur-containing compounds can be in the form of either gas, liquid, or solid. Typical examples of the sulfur-containing co-catalysts are inorganic sulfur compounds such as sulfur monochloride, sulfur dichloride, sodium thiosulfate, potassium thiosulfate, and hydrogen sulfide; alkyl mercaptans such as methyl mercaptan, ethyl mercaptan, n-propyl mercaptane, and n-butyl mercaptan; thiophenols such as thiophenol, p-methyl thiophenol; p-ethyl thiophenol, p-chlorothiophenol, thiohydroquinone, and thionapthol; mercapto-substituted aliphatic carboxylic acids such as thioglicolic acid, thioacetic acid, and thiopropiopionic acid; alkali metal salts of the above-mentioned thiophenols and mercapto-substituted aliphatic carboxylic acids; and mercaptals and mercaptols. These sulfur-containing compounds can be desirably used as a co-catalyst in a mole ratio of 1/2000 to 1/30, based on HCl present in the reaction system.

In the above-mentioned step (A) of the present invention, additional phenol which is supplied to supplement the phenol consumed by the reaction or withdrawal in the reaction system, circulating phenol recovered from the below-mentioned decomposition step (E) of purified p,p'-BPA.PhOH, additional hydrogen chloride or hydrochloric acid which is supplied to supplement the hydrogen chloride or hydrochloric acid consumed by, for example, the withdrawal in the reaction system, and circulating aqueous mother liquor recycled from the below-mentioned mother liquor circulating step (C) are continuously charged as starting materials into the reactor. The mole ratio of the total phenol to the total acetone charged into the reactor is desirably 4 to 20, more desirably 5 to 10, especially to maintain the reaction system to a slurry state and to effect the desired smooth reaction, smooth agitation of the reaction mixture slurry, and sufficient contact of the oil and aqueous phases.

The hydrogen chloride and hydrochloric acid are charged into the reactor in such an amount that the total mole of the hydrochloric acid and hydrogen chloride, in terms of HCl, contained in the reaction mixture is desirably 0.5 to 5 mole based on 1000 g of the reaction mixture in the reactor. This mole ratio is more desirably 1 to 5 mole based on 1000 g of the reaction mixture in the reactor in order to smoothly effect the proceeding of the desired condensation reaction and the conversion of the by-products to p,p'-BPA and to suppress the undesirable accumulation of the by-products in the reaction system. Each above-mentioned starting material is continuously (or in a continuous manner) fed or charged into the reactor. The term "continuously or in a continuous manner" used herein includes that each starting material is fed pulsatively (or in a pulsating flow) so as to maintain the desired ratio of the starting materials in the reaction system. In the practice of the condensation reaction according to the present invention, either a one-vessel type reactor or a multi-vessel type reactor can be used.

In the reaction step (A) of the present invention, the condensation of phenol and acetone, and transformation of the by-products in the circulating mother liquor to p,p'-BPA, and the formation of p,p'-BPA.PhOH adduct are effected. In the condensation reaction of phenol and acetone, the above-mentioned isomer by-products, a small amount of high boiling point by-products, and a trace amount of colored by-products are formed together with the desired p,p'-BPA. Furthermore, p,p'-BPA is also formed from the high boiling point by-products, in addition to the isomer by-products contained in the circulating reaction mother liquid (i.e., the circulating oily mother liquor and the circulating aqueous mother liquor, especially the circulating oily mother liquor). When the above-mentioned condensation reaction and the transformation reaction are carried out while the reaction mother liquor containing the above-mentioned by-products is circulated to the reaction system, the above-mentioned contents in the p,p'-BPA.-PhOH separated from the reaction mixture are remarkably decreased and the conversion percent of the above-mentioned by-products to p,p'-BPA in the reaction system is extremely high. Thus, it is advantageous that the conversion of the by-products to p,p'-BPA is carried out in a heterogeneous reaction condition in which p,p'-BPA is crystallized as p,p'-BPA.PhOH crystals to form a reaction mixture slurry and in which two liquid phases are formed in the reaction mother liquor, as compared with the case where the conversion of the by-products to p,p'-BPA is carried out in a homogeneous reaction condition (i.e., p,p'-BPA is dissolved in the oily mother liquor).

That is, it would seem that, without prejudice to the invention, most of the above-mentioned by-products are dissolved in the oil phase of the reaction mixture slurry since the by-products do not easily form adducts with phenol and, therefore, the isomerization reaction and the transformation reaction proceed to the equilibrium concentration and the resultant p,p'-BPA forms the adduct with phenol to be crystallized. As a result, the above-mentioned isomerization and transformation reactions selectively proceed, whereby the yield of the desired product, p,p'-BPA, is substantially improved. Accordingly, the reaction mixture in the present invention should be in the form of slurry containing the crystallized crude p,p'-BPA.PhOH crystals and the reaction mother liquor in the present invention should be composed of two phases of the oily mother liquor and the aqueous mother liquor.

According to the present invention, the charge conditions of the starting materials to the reactor are set as mentioned above so as to form the desired reaction mixture slurry. Furthermore, the conversion of the acetone is desirably controlled as follows. That is, the condensation reaction is carried out until the conversion of the acetone becomes 90% or more. In order to obtain the reaction mixture slurry having further good properties and to selectively obtain the desired high quality p,p'-BPA at a high yield from the resultant reaction mixture slurry, the reaction is more desirably carried out until the conversion of the acetone becomes 95% or more. The reaction is generally carried out at a temperature of 25° C. to 70° C., desirably 30° C. to 60° C.

In a preferred embodiment of the present invention, the reaction is carried out while at least a portion of the starting materials fed to the reactor is sprayed toward the inner wall of the reactor from feed means such as nozzles provided at the wall of the reactor over the liquid level in the reactor. As a result, the contact conditions of the starting materials are improved and, therefore, the reaction rate is also increased. The starting materials at least a portion of which is sprayed into the reactor are, for example, the starting acetone, the starting phenol, the acidic catalyst and the circulating reaction mother liquor. The desirable amount of the starting material sprayed from the nozzles provided at the reactor is 0.2:1 to 1:1, more desirably 0.4:1 to 1:1, based on the total amount of the starting materials charged into the reactor. The starting materials are desirably sprayed toward the entire inner surface of the reactor from a feed nozzle at the front edge of which plural spray nozzles, optionally a rotatable nozzle or nozzles, are mounted so as to spray the starting materials toward the inner surface of the reactor. Furthermore, the spray feed of at least a portion of the starting materials can also be effected from nozzles provided at a hollow agitator shaft or at an agitator blade through the agitator shaft over the liquid level in the reactor. The sprayed can be effected in any manner, for example, in the form of atomizing, spraying, or jetting, as long as the inner wall surface of the reactor can be sufficiently or effectively washed.

In the separation step (B) of the reaction mixture slurry, the reaction mixture slurry is discharged from the reactor. The reaction mixture slurry discharged from the reactor is separated into the resultant crude p,p'-BPA.PhOH crystals and the two-liquid phase mother liquor by any conventional means such as centrifugal separation, liquid cyclone, and filtration. The crude p,p'-BPA.PhOH crystals contain, as a main constituent, p,p'-BPA.PhOH and contain, as other components, isomer by-products such as o,p'-BPA and o,o'-BPA, high boiling point by-products such as codimer, BPX, o-dimers, dimer of isopropenyl phenol, IPEP cyclic dimer, and IPEP linear dimer, a small amount of by-products such as colored unknown structure by-products, and a trace amount of hydrochloric acid. The by-products contained in the crude p,p'-BPA.PhOH can be decreased by washing the by-products with phenol, aqueous phenol, or hydrochloric acid.

The two-liquid phase reaction mother liquor obtained in the previous separation step (B) of the present invention is further separated into an oily mother liquor and an aqueous mother liquor in the mother liquor circulation step (C) of the present invention. The separated oily mother liquor contains the unreacted and recovered starting phenol used in excess in the reaction, the unreacted acetone, p,p'-BPA dissolved in the phenol, the by-products such as the above-mentioned isomer by-products, the above-mentioned high boiling point by-products, and the above-mentioned colored products, a soluble amount of hydrochloric acid, and the sulfur compound, if used as a co-catalyst. On the other hand, the aqueous mother liquor contains most of the hydrochloric acid recovered from the reactor, the unreacted acetone, a trace amount of p,p'-BPA, a trace amount of the above-mentioned isomer by-products, and the unreacted and recovered starting phenol used in excess in the reaction. The separated oily mother liquor is circulated as a circulating oily mother liquor to the reactor. In this case, although the total amount of the oily mother liquor can be circulated to the reactor, a portion, for example, 2% to 30% by weight, more desirably, 5% to 15% by weight, of the oily mother liquor is desirably discharged from the reaction system to prevent the accumulation or the above-mentioned colored by-products in the reaction system during long-term continuous operation. The remaining oily mother liquor is circulated to the reactor. The discharged oily mother liquor can be treated by any method. Generally, the hydrogen chloride is recovered from the discharged oily mother liquor by an inert gas blowing treatment or a distillation treatment under a reduced pressure. The recovered hydrogen chloride may be used as additional hydrogen chloride in the reaction step (A). The discharged oily mother liquor can also be treated in either of the following manners, after neutralizing with an alkali.

(1) Most of phenol is recovered from the discharged oily mother liquor by, for example, distillation and, then, the still residue is subjected to cracking to separately recover the distilled phenol, p-isopropenyl phenol and tar. The tar is discarded. The recovered p-isopropenyl phenol is addition reacted to phenol in the presence of hydrochloric acid (i.e., addition reaction step) to crystallize p,p'-BPA.PhOH crystals. After the resultant p,p'-BPA.PhOH is separated from the reaction mixture, the separated p,p'-BPA.PhOH can be treated, together with the crude p,p'-BPA.PhOH obtained in the above-mentioned separation step (B) of the reaction mixture slurry, or can be treated alone in the same manner. On the other hand, the separated mother liquor can be treated in the same manner as in the above-mentioned discharged mother liquor and, then, is recycled to the above-mentioned addition reaction step.

(2) The discharged oily mother liquor is concentrated by, for example, distilling off a portion of the phenol, whereby p,p'-BPA.PhOH is crystallized as a crystal. The separated p,p'-BPA.PhOH is treated in the same manner as in the above-mentioned method (1). On the other hand, the separated mother liquor may be discarded or be subjected to a cracking treatment and the subsequent addition reaction as mentioned in the above method (1).

(3) Most of the phenol is recovered from the discharged oily mother liquor by, for example, distillation. The still residue is subjected to cracking, whereby the distilled-off phenol, p-isopropenyl phenol, and tar are separated. The tar is discarded. The recovered p-isopropenyl phenol is addition reacted to phenol in the presence of hydrochloric acid (i.e., an addition reaction step), whereby p,p'-BPA.PhOH is crystallized as a crystalline. The adduct mixture slurry is charged into the reactor in the reaction step (A) or is mixed with the reaction mixture slurry obtained in the separation step (B) to be treated together.

(4) The cracking distillates obtained in the above-mentioned methods (1), (2), and (3) can be directly recycled to the above-mentioned condensation reaction step to be converted into p,p'-BPA.

Furthermore, the aqueous mother liquor separated in the above-mentioned mother liquor circulation step (C) contains water formed by the condensation reaction. When the total amount of the aqueous mother liquor is circulated, water is accumulated in the reaction system. Therefore, a portion of the aqueous mother liquor is withdrawn from the system and the remaining aqueous mother liquor is circulated to the reactor. When the remaining aqueous mother liquor is circulated to the reactor, the weight ratio of the circulating aqueous mother liquor to the circulating oily mother liquor fed to the reactor in the reaction step (A) is desirably 0.01:1 to 2:1, more desirably 0.03:1 to 1.2:1. In order to maintain the reaction rates of condensation and transformation to a moderate range, to maintain the production amount of p,p'-BPA.PhOH per unit volume of the reactor large, to maintain the slurry concentration of the formed reaction mixture slurry, and to economically produce the desired high quality p,p'-BPA.PhOH having a small by-product content, the weight ratio of the circulating aqueous mother liquor to the circulating oily mother liquor is desirably within the above-mentioned range. Furthermore, the hydrogen chloride or concentrated hydrochloric acid can be recovered and be effectively recycled to the above-mentioned reaction step (A) as the additional hydrogen chloride or hydrochloric acid.

In the neutralization and purification step (D) of the crude p,p'-BPA.PhOH according to the present invention, the hydrogen chloride or hydrochloric acid and the above-mentioned by-product impurities contained in the crude p,p'-BPA.PhOH obtained in the separation step (B) of the above-mentioned reaction mixture slurry are removed from the crude p,p'-BPA.PhOH. For this purpose, the crude p,p'-BPA.PhOH is dissolved in a phenol solvent. The phenol solvent is desirably used in an amount that the weight ratio of the phenol solvent to the crude p,p'-BPA.PhOH is 0.1:1 to 10:1, more desirably 0.5:1 to 5:1. The dissolution treatment can be carried out at an ordinary temperature, but the crude p,p'-BPA.PhOH is desirably dissolved in the phenol solvent upon heating. As the phenol solvent, phenol alone may be used, but the use of aqueous phenol (or water-containing phenol) is preferable. The use of the aqueous phenol, as the phenol solvent, having such a composition that the mixture obtained after dissolving the crude p,p'-BAP.PhOH in the aqueous phenol forms a two-liquid phase solution composed of the oil phase solution and the aqueous phase solution is desirable, since the neutralization operation is facilitated and the purification effect becomes large. The phenol content in the aqueous phase is desirably 10% to 65% by weight, more desirably 20% to 60% by weight. When aqueous phenol having a high water content is used as the phenol solvent, the aqueous phenol may be in the form of two liquid phases of an oil phase and an aqueous phase. The dissolution treatment can also be carried out by first dissolving the crude p,p'-BPA.PhOH in phenol, followed by the addition of water in such an amount that the aqueous phenol having the above-mentioned water content is formed. When the dissolved solution forms the two liquid phases, neutral salt compounds such as sodium chloride, potassium chloride, sodium sulfate, potassium sulfate, magnesium sulfate, calcium chloride, ammonium chloride, and magnesium chloride are desirably dissolved in the aqueous phase, in order to suppress the loss of the phenol, the desired p,p'-BPA, and p,p'-BPA.PhOH due to the dissolution thereof in the aqueous phase. The hydrogen chloride or hydrochloric acid contained in the crude p,p'-BPA.PhOH is dissolved in the solution by the above-mentioned dissolution treatment. In the case where the phenol solvent solution of the crude p,p'-BPA.PhOH is a homogeneous solution, the crude p,p'-BPA.PhOH and the hydrogen chloride or hydrochloric acid are dissolved in the solution. Contrary to this, in the case where the phenol solvent solution of the crude p,p'-BPA.PhOH forms a two-liquid phase solution of the oil phase solution and the aqueous phase solution, most of the hydrogen chloride or hydrochloric acid is extracted in the aqueous phase solution and the minor amount of the remaining hydrogen chloride or hydrochloric acid is dissolved in the oil phase solution, whereas most of the crude p,p'-BPA.PhOH is dissolved in the oil phase solution. The hydrogen chloride or hydrochloric acid dissolved in the phenol solvent solution of the crude p,p'-BPA.PhOH is removed therefrom by neutralizing the hydrogen chloride or hydrochloric acid with a base. The base can be added to the phenol solvent prior to the dissolution of the crude p,p'-BPA.PhOH therein or to the phenol solvent solution of the crude p,p'-BPA.PhOH after the dissolution. In either case, the pH of the solution after neutralizatoin is desirably adjusted to 2 to 5, more desirably 3 to 4.5. In the case where the phenol solvent solution of the crude p,p'-BPA.PhOH forms a two-liquid phase mixture as mentioned above, the neutralization can be carried out simultaneously by adding a base to the two-liquid phase mixture or separately by adding a base to the oil phase solution and the aqueous phase solution after the two-liquid phase mixture is separated into the oil phase solution and the aqueous phase solution. Examples of the bases usable in the neutralization are: inorganic bases such as sodium hydroxide, potassium hydroxide, sodium carbonate, potassium carbonate, sodium bicarbonate, potassium bicarbonate, sodium phosphate, magnesium phosphate, potassium phosphate, ammonia, ammonium hydroxide, disodium hydrogen phosphate, dipotassium hydrogen phosphate, dimagnesium hydrogen phosphate, magnesium hydroxide, and calcium hydroxide; organic bases such as sodium phenolate, potassium phenolate, sodium methoxide, and sodium ethoxide, and alkali metal salts of p,p'-BPA. These basic compounds are generally used in the form of an aqueous solution.

After being subjected to the neutralization treatment, the solution of the crude p,p'-BPA.PhOH is treated by any conventional manner such as cooling or concentration. Thus, the p,p'-BPA.PhOH is crystallized. In the case where the solution of the crude p,p'-BPA.PhOH forms a two-liquid phase solution, the above-mentioned crystallization treatment can be applied either to the two-liquid phase solution or the oil phase solution separated from the two-liquid phase solution. However, the latter method is desirable.

The crystallized p,p'-BPA.PhOH thus obtained is separated from the solution, whereby the purified high quality p,p'-PBA.PhOH having a low impurity content of the above-mentioned isomer by-products, high boiling point by-products, and colored by-products can be obtained. The purified p,p'-BPA.PhOH thus obtained has a sufficient high purity. However, the p,p'-BPA.PhOH may be optionally subjected to any conventional purification treatment such as washing or recrystallization.

In the decomposition step (E) of the purified p,p'-BPA.PhOH according to the present invention, the purified p,p'-BPA.PhOH is decomposed to phenol and p,p'-BPA upon heating. The decomposition reaction is generally carried out at a temperature of 100° C. to 200° C., desirably 130° C. to 180° C. Although the pressure of the decomposition reaction also depends upon the decomposition temperature, the decomposition reaction is generally carried out under such a reduced pressure that the phenol formed during the decomposition reaction can be vaporized, for example, under 1 to 500 mmHg, desirably 5 to 300 mmHg.

In the recovery step (F) of the present invention, phenol and p,p'-BPA are recovered from the product obtained from the above-mentioned decomposition step (E), generally from the still residue in the decomposition reaction. When the decomposition reaction of the purified p,p'-BPA.PhOH is carried out in, for example, a distillation column, phenol is recovered from the top of the column and p,p'-BPA is recovered in a molten state from the bottom of the column. The p,p'-BPA thus recovered is of high quality without any purification treatment. The p,p'-BPA is, however, optionally subjected to a purification treatment by, for example, washing the same with water, hot water, weakly acidic hot water, or other solvents. Furthermore, the p,p'-BPA can be purified by recrystallization.

In the recovered phenol circulating step (G) of the present invention, the phenol recovered in the above-mentioned recovery step (F) is circulated to the reactor of the above-mentioned reaction step (A) as a circulating phenol or to the above-mentioned neutralization and purification step (D) as a phenol solvent. Since the phenol is generally recovered in the form of vapor, when the decomposition reaction is carried out under a reduced pressure, the phenol vapor is condensed to be recovered in the form of a liquid.

The production process of high quality p,p'-BPA according to the present invention will now be further illustrated with reference to FIG. 1.

One embodiment of the continuous condensation reaction apparatus used in the practice of the present invention is shown in part (I) of FIG. 1. The starting materials are continuously charged into a series type multi-stage reactor consisting of first, second, and third reactors 11, 12, and 13 of the reaction step (A) from additional starting material tanks 1 and 2, a circulating oily mother liquor tank 3, and a circulating aqueous mother liquor tank 4. The continuous condensation reaction of the reaction step (A) is carried out in the above-mentioned series type multi-stage reactor to form a reaction mixture slurry. The reactor mixture slurry is collected in a receiver 14. The reactor mixture slurry thus obtained is separated into crude p,p'-BPA.PhOH and a two-liquid phase reaction mother liquor is a centrifugal separator 15 of the subsequent separation step (B). The two-liquid phase reaction mixture is separated into an oily mother liquor and an aqueous mother liquor. After portions of the separated oily mother liquor and aqueous mother liquor are optionally discharged or withdrawn from lines 17 and 18, respectively, the remaining mother liquors are recycled to the reactor in the reaction step (A). When the aqueous mother liquor is recycled, the mother liquor is previously saturated or supersaturated with a supplied HCl gas 6 in a HCl absorption vessel 5.

The crude p,p'-BPA.PhOH separated in the centrifugal separator 15 is continuously fed together with a phenol solvent to a dissolving vessel 40 of a continuous neutralization and crystallization apparatus in the neutralization and purification step (D) shown in part (II) of FIG. 1, where the crude p,p'-BPA.PhOH is dissolved in the solvent. Thus, a two-liquid phase solution composed of an oil phase solution and an aqueous phase solution is formed. The two-liquid phase solution thus formed is received and stirred in a tank 41. The oil phase solution from the tank 41 and an alkaline solution from a tank 31 are continuously charged into a neutralizing vessel 42. The mixture is stirred and the pH thereof is adjusted to a predetermined value. The mixture is then separated into an oil phase and an aqueous phase in an oil-water separating vessel. A portion of the aqueous phase solution is withdrawn from a line 33 and the remaining aqueous phase solution is circulated into the dissolving vessel 40. On the other hand, the oil phase solution and fresh phenol from a line 32 are fed to a crystallizing vessel 44 to effect the crystallization. Thus, a mixture slurry is formed. The mixture slurry is separated in a centrifugal separator 46 to separate the mixture slurry into a p,p-BPA.PhOH cake and a mother liquor. The resultant p,p'-BPA.PhOH cake is washed with an aqueous phenol. The washed liquid is combined with the mother liquor and, then, the mixture is separated into the crystallized oily mother liquor and the crystallized aqueous mother liquor in an oil-water separating vessel 47. Portions of the mother liquors thus separated are optionally withdrawn from lines 34 and 35 and the remaining portions are circulated into a crystallizing vessel 44 and a dissolving vessel 40, respectively.

The purified p,p'-BPA.PhOH separated above is continuously charged into a melting vessel 70 in a continuous thermal decomposition apparatus shown in part (III) of FIG. 1. The purified p,p'-BPA.PhOH is dehydrated in a dehydrating column 71 by distilling off water from the top 61 of the column 71. Then, the purified p,p'-BPA.PhOH is fed to a decomposition column 72, wherein the p,p'-BPA.PhOH is decomposed to phenol and p,p'-BPA. The phenol is recovered from the top 62 of the column and the p,p'-BPA is recovered in a molten state as a still residue from the bottom of the column 72.

In the circulation step (G) of the recovered phenol, the recovered phenol is circulated as a circulating phenol to the reactor of the reaction step (A), or is circulated as a phenol solvent to the neutralization and purification step (D). The molten p,p'-BPA obtained as a still residue from the bottom of the decomposition column is adjusted to weak acidity in an oil-water mixing vessel 73 of the recovery step (F) and, then, is mixed with hot water. The mixture is washed in a hot water washing vessel 74 and, then, is crystallized in a crystallization vessel 75. The crystallized p,p'-BPA is separated in a centrifugal separator 76 and is dried in a vacuum dryer 77. Thus, the purified p,p'-BPA crystal is obtained from a line 80.

EXAMPLES

The present invention will now be further illustrated by, but is by no means limited to, the following Examples. In the following Examples and Comparative Examples, the acetone conversion, the amount of HCl contained in 1000 g of a reaction mixture in a reaction system, weight ratio of an aqueous mother liquor to an oily mother liquor, compositions of p,p'-BPA, phenol, water, HCl, and by-products, as well as the quality of purified p,p'-BPA were determined as follows:

1. Quantitative analysis of unreacted acetone

The acetone conversion was determined by measuring the unreacted acetone by means of gas chromatography, after a reaction mixture was dissolved in an ethanol solvent and then neutralized.

2. Quantitative analysis of phenol and p,p'-BPA

Phenol and p,p'-BPA were quantitatively determined by gas chromatography.

3. Quantitative analysis of HCl

HCl was quantitatively determined by a conventional neutralization titration method by dissolving a sample in an ethanol solvent.

4. Quantitative analysis of by-products

By-products were quantitatively determined by an internal standard by means of high speed liquid chromatography, after dissolving the sample in ethanol and then neutralizing it.

5. Determination of colorization degree of circulating oily mother liquor and crude p,p'-BPA.PhOH.

A sample was placed in a measuring cylinder and, then, was diluted with ethanol. The absorbance (or transmission) of the diluted sample filled in a cylindrical glass cell having a light path length of 10 cm was measured at 360 mm and 480 mm in a Spectronic 70 spectrophotometer (manufactured by Bausch & Lomb Co., Ltd.). The sample concentration used in the measurement was appropriately changed depending upon the color of the sample.

The color of the sample was represented by the following equation:

$$E_{1\ cm}^{1\%} = \frac{A}{cb} \qquad (1)^*$$

*Robert M. Silverstein, G. Clayton Bassler (translated by Shun Araki, Yoichiro Mashiko) "Identification Method of Organic Compounds by Spectrum" (Tokyo Kagaku Dojin).

wherein
A = Absorbance
c = Sample concentration (W/V%)
b = Cell length (light path length) (cm)

The $E_{360}$ and $E_{480}$ shown in the Examples and Comparative Examples hereinbelow represent $E_{1\ cm}^{1\%}$ at measurement wavelengths of 360 nm and 480 nm, respectively.

FIG. 2 graphically illustrates the correlation between degree of colorization ($E_{1\ cm}^{1\%} \times 10^4$) at 480 nm (ordinate) and reaction time (time) (abscissa) showing the change at the lapse of time in the degree of colorization of the circulating oily mother liquor and crude p,p'-BPA.PhOH in Example 1 hereinbelow.

6. Determination of weight ratio of an aqueous phase mother liquor to an oily mother liquor in a reaction mixture slurry A reaction mixture slurry discharged from a reactor was placed in a reservoir maintained at the same temperature as in the reactor. After the reaction mixture slurry was filled in the reservoir at a predetermined level, the reaction mixture slurry was charged into a centrifuge maintained at the same temperature as in the reactor and, then, was rotated until the cake was substantially dried. The mother liquor discharged from the centrifuge was introduced into a setting vessel, wherein the mother liquor was separated into the oily mother liquor and the aqueous mother liquor. The volume and specific gravity of each phase were measured and the weight ratio of the aqueous mother liquor to the oily mother liquor was calculated therefrom.

7. Quality examination of purified p,p'-BPA (1) Molten color

Molten color was determined by comparing the color of a molten sample with a Hazen's standard solution immediately after the sample was melted at a temperature of 250° C.

(2) Freezing point

The sample and a thermometer (ASTM 102) were placed in a measurement tube. After cooling in a constant temperature bath at a temperature of 140° C., the freezing point was determined in a conventional manner.

(3) Analysis of organic purities

Analyzed by the same high speed liquid chromatography as used in (4) above.

(4) Determination of degree of colorization $E_{360}$ and $E_{480}$

A sample was diluted to 20 W/V% with ethanol and the absorbance (or transmittance) was determined in the same manner as in (5) above.

EXAMPLE 1

(1) The continuous condensation reaction of acetone and phenol was carried out by using a reaction apparatus shown in FIG. 1.

The first, second, and third reactors as well as the centrifugal separator and oil-water separating vessel were maintained at a temperature of 50° C. A 24.6 g/hr amount of the additional acetone, 143 g/hr of the additional phenol, 1.0 g/hr of the 15% aqueous sodium methyl mercaptate solution, 269 g/hr of the circulating oily mother liquor, 128 g/hr of the circulating aqueous mother liquid, and 5 liter/hr of the additional HCl gas were continuously charged into the first reactor. The reaction mixture discharged from the third reactor was batchwise charged into the centrifugal separator to effect solid-liquid separation. The centrifugally separated cake was used in the below-mentioned neutralization and purification experiment and the separated oily and aqueous mother liquors were recycled to the reactors after excess amounts of the oily and aqueous mother liquors over the above-mentioned feed amounts were withdrawn out of the system.

The compositions of the circulating oily mother liquor and the circulating aqueous mother liquor and the reaction conditions in the continuous reaction are shown in Table 1 below.

TABLE 1

| | | Oily mother liquor | Aqueous mother liquor |
|---|---|---|---|
| Phenol | (wt. %) | 70.3 | 4.2 |
| p,p'-BPA | (wt. %) | 11.7 | 0.1 |
| HCl | (wt. %) | 5.8 | 32.5 |
| Water | (wt. %) | 11.3 | 63.9 |
| Methyl mercaptan | (ppm) | 120 | 30 |
| Reaction conditions | Total phenol/Total acetone in Reaction mixture (mole ratio) | 6.9 | |
| | Additional phenol/Additional acetone (mole ratio) | 3.6 | |
| | Methyl mercaptan/HCl in Reaction mixture (mole ratio) | 1/720 | |
| | HCl/Reaction mixture (mole/1000 g) | 3.7 | |
| | Circulating aqueous mother liquor/Circulating oily mother liquor (wt. ratio) | 0.46 | |
| | Discharge percent of oily mother liquor (wt. %) | 10 | |
| | Discharge percent of aqueous mother liquor (wt. %) | 3.2 | |

The continuous reaction was carried out for 350 hours. As shown in FIG. 2, the $E_{480}$ values representing the degree of colorization of the oily mother liquor and the centrifugally separated cake were increased with the lapse of time until the reaction time of 300 hours. However, the increase curve of the $E_{480}$ values was saturated (i.e., No further increase in the $E_{480}$ values was substantially recognized) after the reaction time exceeded 300 hours. Likewise, the contents of the by-products contained in the oily mother liquor and the centrifugally separated cake (i.e., crude p,p'-BPA.-PhOH) became constant. The contents of the by-products, HCl, and $H_2O$ contained in the circulating oily mother liquor and the centrifugally separated cake are shown in Table 2.

TABLE 2

| | Circulating oily mother liquor (wt %) | Centrifugally separated cake (wt %) |
|---|---|---|
| o,p'-BPA | 0.743 | 0.052 |
| BPX | 0.052 | Not detected |
| Codimer | 0.028 | " |
| Other by-products | 0.402 | 0.042 |
| HCl | 5.8 | 0.34 |
| $H_2O$ | 11.3 | 1.2 |

The conversion of the acetone in this reaction was 99%, and the overall yield of p,p'-BPA based on the acetone over 350 hours was 99.5 mole%.

(2) The continuous neutralization and crystallization of crude p,p'-BPA.PhOH obtained in the continuous condensation reaction were carried out as follows.

The p,p-BPA.PhOH obtained above was charged at a rate of 500 g/hr into the dissolving vessel kept at 70° C. and, then, 1000 g/hr of the below-mentioned neutralization system circulating aqueous mother liquor and 320 g/hr of the below-mentioned crystallization oily mother liquor were charged into the dissolving vessel. The mixture was thoroughly stirred. The resultant two-liquid phase solution consisting of an oil phase solution containing the completely dissolved p,p'-BPA.PhOH and an aqueous solution was charged into the neutralization vessel. In the neutralization vessel, 37 ml/hr of a 18% aqueous NaOH solution was continuously fed to control the pH of the neutralized aqueous phase to 4 (weak acidity). Then, the neutralized product was fed to the oil-water separating vessel to separate it into an oil phase and an aqueous phase. The separated aqueous phase was reused as a circulating aqueous phase in the neutralization system. When the separated aqueous phase was recycled, 1000 g/hr of the circulating aqueous phase was recycled and the remaining aqueous phase was withdrawn as waste water from the neutralization system.

On the other hand, the oil phase, discharged from the oil-water separation vessel, fresh phenol, and an oil phase of the below-mentioned crystallization mother liquor were continuously introduced into the crystallization vessel. The mixture was thoroughly mixed. The mole ratio of p,p'-BPA to phenol to 2.5 was adjusted in the crystallization vessel. Furthermore, an aqueous phase of the below-mentioned crystallization mother liquor was continuously fed from another feed nozzle to the crystallization vessel. Thus, the continuous crystallization was carried out in the crystallization vessel. The resultant slurry mixture was collected in a receiver and, then, the slurry mixture was centrifugally separated once every 30 minutes in the warmed centrifuge to the solid phase and the liquid phase. The p,p'-BPA.PhOH thus obtained in the form of a cake was further rinsed with an aqueous phenol solution to obtain 237 g of the purified p,p'-BPA.PhOH (per 30 minutes). On the other hand, the crystallization mother liquor obtained from the solid-liquid separation of the above-mentioned slurry mixture and the washing liquid were collected in the oil-water separation vessel to separate into an oil phase and an aqueous phase. These oil phase and aqueous phase were reused as the above-mentioned crystallization oily mother liquor and crystallization aqueous mother liquor.

The quality of the purified p,p'-BPA.PhOH thus obtained is shown in Table 3.

TABLE 3

| Concentration (wt. %) of organic impurities | |
|---|---|
| o,p'-BPA | 0.004 |
| BPX | Not detected |
| Codimer | 0.003 |
| Other by-products | 0.017 |
| Transmittance (E value) | |
| $T_{360}$ ($E_{360}$) at 360 nm | 68% ($8.3 \times 10^{-4}$) |
| $T_{480}$ ($E_{480}$) at 480 nm | 93% ($1.6 \times 10^{-4}$) |
| Molten color (APHA) | 25 |

(3) The removal of phenol from the above-mentioned purified p,p'-BPA.PhOH and the production of p,p'-BPA.PhOH were carried out as follows.

A 500 g/hr amount of the purified p,p'-BPA.PhOH was melted under a nitrogen gas atmosphere in a flask and, then, the molten p,p'-BPA.PhOH was charged into a warmed double tube type cylinder. The molten p,p'-BPA.PhOH was introduced at a feed rate of 250 g/hr into the dehydration column and, then, was dehydrated at a temperature of 140° C. under 100 mmHg. The dehydrated molten product was continuously discharged from the bottom of the dehydration column and was immediately fed to the phenol recovery column. As the dehydration column, a distillation column provided with 10 sieve trays was used and the dehydrated molten product from the dehydration column was fed to the forth tray from the bottom. The phenol recovery distillation column was operated such that the temperature of the column bottom flask was 163° C. under 20 mmHg. A 67.2 g/hr amount of the recovered phenol was obtained from the top of the column and the recovered phenol was reused as the additional phenol in the above-mentioned continuous condensation reaction.

On the other hand, 174.8 g/hr of the molten p,p'-BPA was obtained from the bottom of the phenol recovery column. Then, the molten p,p'-BPA thus obtained and hot water adjusted to weak acidity were continuously charged into the oil-water mixing vessel to thoroughly mix the p,p'-BPA with water. The mixture thus obtained was charged into the hot water washing vessel while thoroughly stirring. After thoroughly washing while stirring, the oil phase and the aqueous phase were separated in the settling chamber. Thus, 233.3 g/hr of the separated oil phase was continuously discharged. The oil phase containing, as a main constituent, p,p'-BPA discharged from the hot water washing vessel and weak acidic hot water were charged into the crystallization vessel while mixing. The continuous crystallization was carried out while stirring. The slurry mixture thus obtained was introduced into a receiver and a wet cake was separated from the slurry mixture in the warmed centrifuge once an hour. Thus, 173.3 g/hr of the wet cake was obtained.

The wet cake was then placed in the vacuum dryer and, then, was dried under heating and reduced pressure conditions. Thus, 167.3 g/hr of the purified p,p'-BPA was obtained.

The quality of the resultant purified p,p'-BPA is shown in Table 4.

TABLE 4

| Quality of Purified p,p'-BPA | |
|---|---|
| Concentration (wt. %) of organic impurities | |
| Phenol | 0.008 |
| o,p'-BPA | Not detected |
| BPX | " |
| Codimer | 0.003 |

TABLE 4-continued

| Quality of Purified p,p'-BPA | |
|---|---|
| Other by-products | 0.023 |
| Transmittance (E Value) | |
| $T_{360}$ ($E_{360}$) at 360 nm | 68% (8.4 × 10$^{-4}$) |
| $T_{480}$ ($E_{480}$) at 480 nm | 94% (1.2 × 10$^{-4}$) |
| Molten color (APHA) | 25 |
| Freezing point | 156.6° C. |

EXAMPLES 2 TO 11

A series of continuous experiments was carried out by using the reaction apparatus shown in FIG. 1 in the same manner as in Example 1, except that the experimental conditions were changed in each Example as listed in Table 5 below. The quality of the purified p,p'-BPA thus prepared was evaluated as in Example 1. In Examples 2 to 11, the production of the purified p,p'-BPA from the crude p,p'-BPA.PhOH was carried out in the same manner as in Example 1. Portions of the continuous reaction conditions different from those of Example 1 were listed in Table 5.

In Examples 2 and 3, the continuous reaction conditions were set so that the mole ratios of total phenol to total acetone in the reaction systems became 6/1 (Example 2) and 10/1 (Example 3), respectively.

The continuous experiments were carried out while the reaction another liquor was circulated in the same manner as in Example 1.

In Examples 4 and 5, the continuous reaction conditions were set so that the mole numbers of HCl contained in 1000 g of the reaction mixture in the continuous reaction systems became 1 mole (Example 4) and 5 moles (Example 5), respectively, while the reaction mother liquors were circulated in the same manner as in Example 1.

In Examples 6 and 7, the continuous reaction conditions were set so that the reaction temperature in the continuous reaction systems became 60° C. (Example 6) and 40° C. (Example 7), respectively, while the reaction mother liquors were circulated in the same manner as in Example 1.

In Examples 8 and 9, the continuous reactions were set so that the average residence times in the continuous reactor became 4 hours (Example 8) and 6 hours (Example 9), respectively, while the reaction mother liquors were circulated in the same manner as in Example 1.

In Examples 10 and 11, the continuous reaction conditions were set so that the weight ratios of the aqueous mother liquors to the oily mother liquors in the reaction mixture slurry became 0.03 (Example 10) and 1.2 (Example 11), respectively, by changing the amounts of the aqueous hydrochloric acid phases fed to the reactors, while the reaction mother liquors were circulated in the same manner as in Example 1.

The results obtained from 350 hours' continuous reactions in Examples 2 to 11 as well as the quality evaluation results of the purified p,p'-BPA.PhOH and p,p'-BPA are shown in Table 5.

TABLE 5

| | Example No. | | | | | | | | | | |
|---|---|---|---|---|---|---|---|---|---|---|---|
| Reaction conditions different from Example 1 | 2 | 3 | 4 | 5 | 6 | 7 | 8 | 9 | 10 | 11 | |
| | Total phenol/Total acetone (mole ratio) | | HCl mole/1000 g reaction mixture | | Reaction Temp. | | Average residue time | | | Aqueous phase/Oil phase (wt. ratio) | |
| | 6/1 | 10/1 | 1 mole | 5 mole | 60° C. | 40° C. | 4 hr | 6 hr | | 1.2 | |
| Yield of crude p,p'-BPA.PhOH in continuous condensation reaction (mole %) | 99.0 | 99.5 | 98.0 | 99.0 | 99.5 | 99.0 | 98.5 | 99.5 | 99.5 | 99.5 | |
| Concentration (wt. %) of Organic Impurities in Purified p,p'-BPA.PhOH | | | | | | | | | | | |
| o,p'-BPA | 0.005 | 0.003 | 0.008 | 0.004 | 0.003 | 0.005 | 0.006 | 0.004 | 0.004 | 0.004 | |
| BPX | Not detected | Not detected | Not detected | Not detected | Not detected | Not detected | Not detected | Not detected | Not detected | Not detected | |
| Codimer | 0.004 | 0.002 | 0.005 | 0.004 | 0.002 | 0.003 | 0.004 | 0.003 | 0.003 | 0.003 | |
| Other impurities | 0.023 | 0.015 | 0.030 | 0.018 | 0.016 | 0.023 | 0.020 | 0.019 | 0.017 | 0.017 | |
| Transmittance | | | | | | | | | | | |
| $T_{360}\%$ ($E_{360}$) | 68($8.3 \times 10^{-4}$) | 69($8.1 \times 10^{-4}$) | 68($8.3 \times 10^{-4}$) | 68($8.3 \times 10^{-4}$) | 66($9.0 \times 10^{-4}$) | 69($8.1 \times 10^{-4}$) | 67($8.7 \times 10^{-4}$) | 68($8.3 \times 10^{-4}$) | 68($8.3 \times 10^{-4}$) | 68($8.3 \times 10^{-4}$) | |
| $T_{480}\%$ ($E_{480}$) | 94($1.2 \times 10^{-4}$) | 94($1.2 \times 10^{-4}$) | 94($1.2 \times 10^{-4}$) | 93($1.6 \times 10^{-4}$) | 92($1.8 \times 10^{-4}$) | 95($1.1 \times 10^{-4}$) | 93($1.6 \times 10^{-4}$) | 94($1.2 \times 10^{-4}$) | 93($1.6 \times 10^{-4}$) | 93($1.6 \times 10^{-4}$) | |
| Molten color (APHA) | 25 | 20 | 25 | 25 | 30 | 20 | 30 | 25 | 25 | 25 | |
| Quality of Purified p,p'-BPA | | | | | | | | | | | |
| Concentration (wt. %) of Organic Impurities | | | | | | | | | | | |
| Phenol | 0.008 | 0.007 | 0.008 | 0.009 | 0.007 | 0.008 | 0.007 | 0.008 | 0.007 | 0.008 | |
| o,p'-BPA | Not detected | Not detected | Not detected | Not detected | Not detected | Not detected | Not detected | Not detected | Not detected | Not detected | |
| BPX | " | " | " | " | " | " | " | " | " | " | |
| Codimer | 0.003 | 0.002 | 0.002 | 0.004 | 0.003 | 0.003 | 0.002 | 0.003 | 0.003 | 0.004 | |
| Other impurities | 0.023 | 0.021 | 0.022 | 0.028 | 0.022 | 0.023 | 0.022 | 0.021 | 0.022 | 0.025 | |
| Transmittance | | | | | | | | | | | |
| $T_{360}\%$ ($E_{360}$) | 68($8.3 \times 10^{-4}$) | 70($7.7 \times 10^{-4}$) | 69($8.3 \times 10^{-4}$) | 69($8.3 \times 10^{-4}$) | 67($8.7 \times 10^{-4}$) | 70($7.7 \times 10^{-4}$) | 67($8.7 \times 10^{-4}$) | 69($8.1 \times 10^{-4}$) | 68($8.3 \times 10^{-4}$) | 69($8.1 \times 10^{-4}$) | |
| $T_{480}\%$ ($E_{480}$) | 94($1.2 \times 10^{-4}$) | 95($1.1 \times 10^{-4}$) | 94($1.2 \times 10^{-4}$) | 94($1.2 \times 10^{-4}$) | 93($1.8 \times 10^{-4}$) | 95($1.1 \times 10^{-4}$) | 93($1.6 \times 10^{-4}$) | 95($1.1 \times 10^{-4}$) | 94($1.2 \times 10^{-4}$) | 95($1.1 \times 10^{-4}$) | |
| Molten color (APHA) | 25 | 20 | 25 | 25 | 30 | 20 | 30 | 25 | 25 | 25 | |
| Freezing point (°C.) | 156.6* | 156.7 | 156.6 | 156.6 | 156.6 | 156.7 | 156.6 | 156.6 | 156.6 | 156.6 | |

COMPARATIVE EXAMPLE 1

The following experiment was carried out by using the continuous condensation reaction apparatus shown in FIG. 1.

The continuous condensation reaction was carried out in the same manner as in Example 1, except that the aqueous mother liquor was entirely recycled without withdrawing a portion of the aqueous mother liquor obtained from the continuous reaction from the system. As a result, since water formed in the condensation reaction was gradually accumulated in the reaction system, the continuous reaction could not substantially be continued while maintaining the predetermined reaction conditions. Accordingly, the continuous reaction was continued by gradually increasing the amount of the circulating aqueous mother liquor according to the increasing rate from 30 hours after the beginning of the reaction.

As a result, the residence time in the reaction system became gradually short and, accordingly, the acetone conversion was decreased, as shown in Table 6.

TABLE 6

| | Results of Continuous Operation | | |
|---|---|---|---|
| Running time (hr) | Residence time (hr) | Acetone conversion (%) | Weight ratio of aqueous phase/oil phase |
| 50 | 4.6 | 99 | 0.6 |
| 250 | 3.4 | 95 | 1.2 |
| 500 | 2.6 | 85 | 2.1 |

As shown in Table 6, when the continuous reaction was continued while increasing the circulating amount of the aqueous mother liquor, the residence time became 2.6 hours, which was about ½ of Example 1, at an operation time of 500 hours and the acetone conversion was decreased to 86%. Furthermore, the weight ratio of the aqueous phase to the oil phase in the reaction mixture became 2.1. Thus, the intended reaction could not be continued under the desired reaction conditions when the reaction time reached 500 hours.

COMPARATIVE EXAMPLE 2

The continuous condensation reaction of Example 1 was repeated to prepare p,p'-BPA, except that the crude p,p'-BPA.PhOH obtained after 300 hours' reaction was directly melted without a neutralizing and purifying treatment.

The quality of p,p'-BPA thus prepared is shown in Table 7.

TABLE 7

| Quality | |
|---|---|
| Organic impurities (wt. %) | |
| Phenol | 0.010 |
| o,p'-BPA | 0.004 |
| BPX | Not detected |
| Codimer | 0.003 |
| Other by-products | 0.054 |
| Molten color (APHA) | 120 |
| Freezing point | 156.5° C. |

As is clear from the comparison of the above-mentioned Examples and Comparative Examples, according to the present invention, p,p'-BPA having higher quality can be selectively and economically produced at a high yield. This is an extremely remarkable effect taking into consideration the application fields of p,p'-BPA and conventional many improved processes for producing p,p'-BPA.

We claim:

1. A process for continuously producing high quality 2,2-bis(4-hydroxyphenyl)propane from a reaction of phenol and acetone in the presence of a hydrochloric acid containing catalyst comprising the steps of:

(A) carrying out said reaction by continuously charging additional phenol, the below-mentioned circulating phenol, additional acetone, additional hydrogen chloride or hydrochloric acid, the below-mentioned circulating oily mother liquor, and the below-mentioned aqueous phase mother liquid, into a reactor to form a reaction mixture slurry comprising the crude phenol adduct of 2,2-bis(4-hydroxyphenyl)propane in the form of crystal and two liquid phase reaction mother liquors of an oily mother liquor and an aqueous mother liquor;

(B) separating said reaction mixture slurry into the crude phenol adduct of 2,2-bis(4-hydroxyphenyl)propane and the two liquid phase mother liquors after discharging the reacting mixture slurry from the reactor;

(C) separating said two liquid phase mother liquors obtained in the above-mentioned step (B) into the oily mother liquor and the aqueous mother liquor, whereby the oily mother liquor is circulated as a circulating oily mother liquor to the reactor and the remaining portion of the aqueous mother liquor, after discharging a portion thereof, is circulated as a circulating aqueous mother liquor to the reactor;

(D) dissolving said crude phenol adduct of 2,2-bis(4-hydroxyphenyl)propane obtained in the above-mentioned step (B) in a phenol solvent and, after neutralizing the hydrogen chloride or hydrochloric acid contained in the crude phenol adduct with a base, crystallizing and separating the phenol adduct of 2,2-bis(4-hydroxyphenyl)propane from the solution to obtain the purified phenol adduct of 2,2-bis(4-hydroxyphenyl)propane;

(E) decomposing said purified phenol adduct of 2,2-bis(4-hydroxyphenyl)propane obtained in the above-mentioned step (D), on heating, at a temperature in the range of 100° C. to 200° C. and a pressure of 1 to 500 mm Hg, to form a thermally decomposed product containing phenol and 2,2-bis(4-hydroxyphenyl)propane;

(F) recovering the phenol and 2,2-bis(4-hydroxyphenyl)propane from said thermally decomposed product obtained in the above-mentioned step (E); and (G) circulating said phenol recovered in the above-mentioned step (F) to a reactor in the above-mentioned step (A) as a circulating phenol or to the above-mentioned step (D) as a phenol solvent.

2. A process as claimed in claim 1, wherein the remaining portion of the oily mother liquor, after discharging a portion thereof, is circulating as a circulating oily mother liquor when the oily mother liquor is circulated in the above-mentioned step (C).

3. A process as claimed in claim 1, wherein the phenol solvent used in the above-mentioned step (D) is an aqueous phenol having such a composition that two liquid phases comprising the oil phase and the aqueous phase are formed when the crude phenol adduct of 2,2-bis(4-hydroxyphenyl)propane is dissolved in the phenol solvent.

4. A process as claimed in claim 1, wherein the 2,2-bis(4-hydroxyphenyl)propane recovered in the above-mentioned step (F) is further washed with hot water.

5. A process as claimed in claim 1, wherein the decomposition reaction temperature in step (E) is from 130° C. to 200° C.

6. A process as claimed in claim 1 wherein the decomposition reaction and the recovering steps (E) and (F) are carried out in a distillation column.

* * * * *